(12) United States Patent
Fukui et al.

(10) Patent No.: US 6,596,540 B2
(45) Date of Patent: Jul. 22, 2003

(54) METHOD FOR INTRODUCTION OF AN EXOGENOUS GENETIC SUBSTANCE OR A PHYSIOLOGICALLY ACTIVE COMPOUND

(75) Inventors: Kiichi Fukui, Osaka (JP); Akio Kobayashi, Toyonaka (JP); Satoshi Harashima, Takatsuki (JP); Eiichiro Fukusaki, Suita (JP); Takefumi Sone, Suita (JP)

(73) Assignee: Osaka University, Osaka (JP)

( * ) Notice: Subject to any disclaimer, the term of this patent is extended or adjusted under 35 U.S.C. 154(b) by 0 days.

(21) Appl. No.: 09/956,166

(22) Filed: Sep. 20, 2001

(65) Prior Publication Data
US 2002/0081737 A1 Jun. 27, 2002

(51) Int. Cl.[7] .......................... C12N 15/00; A61K 9/14; A61K 48/00
(52) U.S. Cl. .................. 435/455; 424/422; 424/484; 424/486; 424/489; 424/490; 424/491; 514/44
(58) Field of Search .................. 435/455; 424/422, 424/484, 486, 489, 490, 491; 514/44

(56) References Cited

U.S. PATENT DOCUMENTS

| | | | | |
|---|---|---|---|---|
| 4,713,245 A | * | 12/1987 | Ando et al. .................. | 424/438 |
| 4,747,881 A | * | 5/1988 | Shaw et al. .................. | 106/209 |
| 5,164,188 A | * | 11/1992 | Wong .......................... | 424/428 |
| 5,466,587 A | * | 11/1995 | Fitzpatrick-McElligott et al. ........................ | 435/172.1 |

FOREIGN PATENT DOCUMENTS

WO    WO 93/08292    *   4/1993

OTHER PUBLICATIONS

Wan et al., Surfactant effects on alginate microspheres, 1994, International Journal of Pharmaceutics, vol. 103, pp. 267–275.*

Quong et al., External versus internal source of calcium during the gelation of alginate beads for DNA encapsulation, 1997, Biotechnology Bioengineering, vol. 57, pp. 438–446.*

You et al., Drug release characterization and preparation of Ca–alginate microparticle drug carrier using membrane emulsification method, 1999, Hwahak Konghak, vol. 37, pp. 789–794.*

Tin et al., DNA encapsulation by an air–agitated, liquid–liquid mixer, 1997, Biotechnology Bioengineering, vol. 56, pp. 464–470.*

* cited by examiner

*Primary Examiner*—James Ketter
*Assistant Examiner*—Daniel M. Sullivan
(74) *Attorney, Agent, or Firm*—Burns, Doane, Swecker & Mathis, LLP

(57) ABSTRACT

A novel method for introduction of an exogenous substance or a physiologically active compound into cells is provided according to this invention. This method can realize introduction of an exogenous genetic substance or a physiologically active compound of large size with a large amount. Such substance is immobilized to beads of sphere fine particles having a particle size of 0.01 mm to 10 mm, and bio-active beads thus produced are introduced into cells. Bio-active beads comprising calcium alginate are particularly useful for the purpose of the present invention.

8 Claims, 6 Drawing Sheets

(6 of 6 Drawing Sheet(s) Filed in Color)

US 6,596,540 B2

METHOD FOR INTRODUCTION OF AN EXOGENOUS GENETIC SUBSTANCE OR A PHYSIOLOGICALLY ACTIVE COMPOUND

BACKGROUND OF THE INVENTION

1. Field of the Invention

This invention relates to a novel method for introduction of an exogenous genetic substance or a physiologically active compound into a cell.

2. Prior Art

Heretofore, as a method for introduction of an exogenous gene into a cell, electroporation, particle gun, Agrobacterium-mediated gene transfer and such have been utilized. In the case of electroporation and particle gun, small pores on the cell are opened transiently and the genetic substances are introduced into the cell. Agrobacterium mediated gene transfer system utilizes bacterial infection to introduce exogenous gene. Considering the aspect of these methods, large amount or large size of genes can be hardly introduced into the cells. Thus, the range of genes or genetic substances introduced by the conventional methods is limited.

SUMMARY OF THE INVENTION

There have been demands on development of a novel method for gene introduction. That is, such novel method should enable introduction of an exogenous gene at a larger amount than the conventional methods, and further enable introduction of a large-sized gene, which has never been introduced by the conventional methods. It is an object of the present invention to provide a method for gene introduction, which can overcome such defects. Moreover, the method of the present invention can be used to introduce various physiologically active compounds into a plant.

The present inventors prepared beads having the shape of fine spherical particles and immobilized genetic substance into the beads. Then they have tried introduction of gene using such method. Incidentally, in the present specification, immobilization of an exoegnous genetic substance or a physiologically active compound means that the genetic substance or the physiologically active compound is retained inside or on the surface of the formed gel. The size of the beads of the present invention is preferably from 0.01 $\mu$m to 10 $\mu$m. Therefore, by using the beads of the present invention, a large amount of gene can be introduced all at once, as compared with the conventional methods. Furthermore, according to the present invention, it is possible to introduce a gene of large size or a genetic substance such as mRNA, plasmid DNA and artificial chromosomes, which could not be introduced by the conventional techniques.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

The present invention will be further explained in detail hereafter with reference to the accompanying drawings, in which.

DESCRIPTION OF THE PREFERRED EMBODIMENTS

Figure 1:
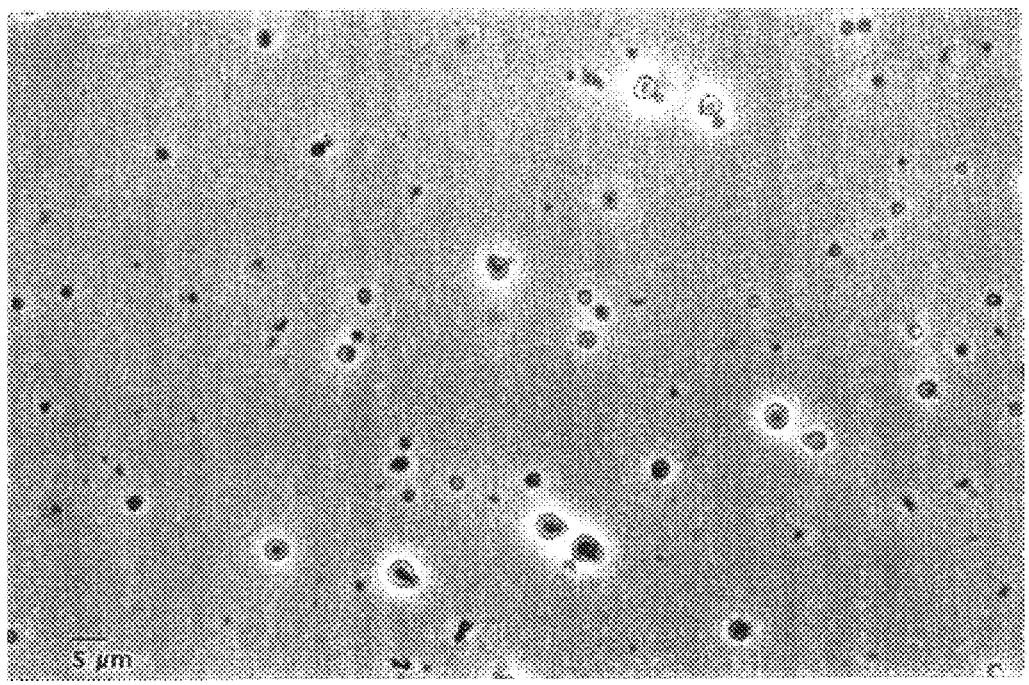
FIG. 1 is a photograph of bio-active beads of the present invention taken by phase contrast microscope.

As the preferred material for the beads of the present invention, aqueous solution of alginate monovalent salt, k-carrageenan and polysaccharide, such as agar and gellan gum, can be exemplified. Gel formation of alginate monovalent salt, k-carrageenan and gellan gum can be controlled by the species of the ionic molecules. Moreover, agar and gelatin are water-soluble compounds which can form gel. Micro meter-sized beads can be constructed with W/O (water/oil) type emulsion. The aqueous solution of alginate monovalent salt or the like, which contains physiologically active compound or an exogenous genetic substance can be mixed with some water-nonmiscible organic solvent. The mixture can be suspended by sonication treatment, whereby W/O type emulsion with a particle size of 0.01 to 10 $\mu$m can be formed. Aqueous solution containing a divalent cation or other multivalent cations can be immediately added to the above mentioned emulsion, then gel formation is performed to form beads, having particle size of 0.01 to 10 $\mu\mu$m and containing genetic substance inside thereof or at the surface thereof. If the exogenous genetic substance or the physiologically compound is damaged by sonication treatment, it can be dissolved in an aqueous solution containing the cation, then the gel formation is performed to form beads.

In concrete, small bio-active beads of calcium alginate can be prepared as the bio-active beads of the present invention. This method utilizes solidification of alginate triggered by divailent calcium ion. When an emulsion of alginate in W/O type emulsion system is formed, calcium chloride is added to the emulsion, then both are mixed to prepare the bio-active beads according to this method. Furthermore, the alginate solution can be formed to fine liquid drops by using a cell sorter, and dropped into the calcium chloride solution to prepare the bio-active beads. In this specification, "solidification material" means a material of solidification, such as sodium alginate. Moreover, "solidification agent" means an agent that triggers solidification of the material, such as calcium ion. Moreover, "solidification product" means a product produced as a result of solidification, such as calcium alginate. However, the solidification material, the solidification agent and the solidification product are not to be limited to compounds described above, but intended to include other compounds having equivalent properties.

The methods such as electroporation, polyethyleneglycol-mediated gene transfer, micro-injection, pin-point delivery using optical tweezers and such can be adopted to introduce the bio-active beads produced with the method of this invention. Using methods such as described above, the bio-active beads can be easily introduced into plant cells, as well as into animal cells. The plant cells can have pores, which are physically produced using tools such as needle or beam irradiation. Otherwise, cell wall of the plant cells can be removed by some enzymatic treatment. According to this method, introduction can be performed under a very mild condition for the enclosure. Therefore, introduction of large-sized genetic substances, such as chromosomes or nucleus, can be performed without causing damage, An aqueous solution of sodium alginate, at a concentration of 0.5% to 3%, can be dropped to calcium chloride aqueous solution of about 50 mM. Then, semitransparent gels having a gravity higher than that of water can be prepared. At preparation of the bio-active beads of the present invention, the concentration of sodium alginate is preferably 0.5% to 3%, and the concentration of calcium chloride is preferably 50 mM to 100 mM. Moreover, the organic solvent used to emulsify the bio-active beads is preferably isoamyl alcohol or butanol. When the concentration of sodium alginate is lower than 0.25%, or when the concentration of calcium chloride is lower than 25 mM, gelation of sodium alginate can not be achieved and the beads of the invention can not be prepared. When the concentration of calcium chloride is higher than 500 mM and the concentration of calcium alginate is lower than 0.5%, semispherical beads of large size are likely to be formed and they do not have a complete spherical shape. Moreover, when the concentration of sodium alginate is higher than 3%, the size of liquid drops do not reach to a sufficient large size at the time of preparation of the emulsion. Then beads having shapes like rear drops tend to be formed. Beads having a practically applicable size (10 $\mu$m to 0.1 $\mu$m) can be formed when the concentration of sodium alginate is from 0.5 to 1.5% and the concentration of calcium chloride is from 50 to 200 mM. Moreover, the beads are suspended into an aqueous solution of 10 mM calcium chloride, then they are placed on a Nylon mesh with a pore size of 5 $\mu$m. They are filtered with centrifugation at 5000 rpm for 5 minutes to remove particles larger than 5 $\mu$m, whereby beads having a size smaller than 5 $\mu$m can be collected.

The beads thus obtained rapidly alters to its sol form in a solution containing EDTA or EGTA, which chelate a divalent cation, or in a solution containing a high concentration of monovalent cation. Therefore, the beads should be preserved in an aqueous solution of 10 mM calcium chloride. Moreover, when the concentration of calcium chloride is higher than 1 M, the beads tend to form aggregate, which makes re-suspension of the beads difficult. In the case that centrifugation for recovery of the beads is performed at a speed higher than 7000 rpm, the beads also tend to form aggregate and resuspension of the beads becomes difficult.

The present inventors thought that adopting a method with optical tweezers might enable good operationality, at introduction of an exogenous genetic substance into a cell. Then they have reviewed the requirements for bio-active beads, which can be used for such purpose. That is, they have performed investigations on what kinds of materials are suitable for the bio-active beads as a carrier retaining DNA, As a result, the following requirements are listed as the requisite factors for the bio-active beads of the present invention.

(1) Before solidification, the material should be dissolved in a solution, in which DNA is dissolved or suspended. Moreover after solidification, the material should form a solid or a gel, which is stable in an aqueous solution to some extent.

(2) To realize operation with optical tweezers, the beads should transmit light and have a refractive index higher than that of water.

(3) The beads should have a relative density similar to or slightly higher than that of water.

(4) The procedure of operation should be easy.

(5) The beads should be prepared by conventional materials and devices.

(6) The beads should not inhibit growth of a cell.

(7) In the course of preparation of beads and after solidification, DNA should be maintained stably inside of the beads.

(8) To be introduced into a cell, the beads should be prepared to a diameter smaller than 10 $\mu$m.

(9) In a cell, the beads should release exogenous DNA.

The present inventors have investigated on these points. As a result, bio-active beads of calcium alginate satisfied all the requirements as mentioned above. More specifically, bio-active beads composed of calcium alginate of the present invention were stable at room temperature in water of neutral pH. To study whether these gels affect on growth of a cell, gels in which seeds of Arabidopsis were encapsulated were placed in water and germination after 2 or 3 days was examined. As a result, decrease in the germination ratio was not recognized, as compared with the case that seeds were seeded on wet filter papers, which is the usual condition. It should be noted that, alginate has been conventionally used as a food additive, indicating its high safety. Moreover, alginate has been used in techniques of cell immobilization, as an excellent support medium for cells.

For a conventional method, an exogenous genetic substance or a physiologically active compound can be mixed, prior to preparation of an emulsion. In this method, the exogenous genetic substance or the physiologically active compound exists when the preparation of emulsion is performed. Therefore, it is difficult to retain a substance having a high molecular weight. On the other hand, in the method of the present invention, a genetic substance is fixed to the beads after preparation of emulsion, utilizing hydrophilic property of the material. Then preparation of the beads can be performed under extremely gentle conditions. Thus, this method enables introduction of exogenous genetic substances having large size, such as chromosomes, artificial chromosomes, organellas or nucleus. According to the conventional techniques, it has been difficult to introduce these substances without causing damages. Therefore, the bio-active beads of the present invention are useful as a novel technique for transformation of wide range of living creatures.

Moreover, gelatin-agarose type bio-active beads can be prepared and utilized for the purpose of the present invention. This method utilizes gelation of gelatin and agarose. According to this method, the gelatin-agarose type bio-active beads can be prepared by adding drops of suspension, melting the suspension by heating, emulsifying in an organic solvent-water emulsion system, succeeded by solidification by cooling. Moreover, a sol melted by heating can be sprayed under a low temperature and momentary preparation of a gel can be achieved.

Moreover, vinyl polymer type bio-active beads can be prepared and utilized for the purpose of the present invention. In this method, an emulsion polymerization system (toluene-water) of an acrylic monomer, such as styrene type monomer, acrylic type monomer or methacrylic type monomer can be adopted. Then, polymerization agent, such as sodium peroxodisulfate (APS), can be added to the system for solidification. When sheet polymerization is performed, it would be possible to control the size of particles to some extent. In the vinyl monomer system bio-active beads multilayer structure can be formed so that DNA can be included between the layers.

Moreover, hydrogel type bio-active beads can be also prepared. The acrylester type or acrylamide type of sheet-shaped hydrogel can be prepared. After performance of dehydration and shrinkage, it can be subjected to cutting at a size of approximately several mm. As a means to have the material polymerized in a shape of thin sheet, photo-polymerization can be performed after development of a monomer solution on a non-aqueous solvent, such as octane or heptane. To control its thickness, a suitable organic solvent, such as alcohol, can be added to aqueous solution of a monomer adjust its surface tension. After polymerization, it can be scooped up on a suitable support and it can be subjected to processing after drying. As a method for processing, laser processing, as well as machine processing can be performed, that is, processing according to these physical crushing methods can be performed. Moreover, hydrogel type bio-active can be prepared, according to spraying method. According to the spraying method, at preparation of a solution of prepolymer containing DNA, ultraviolet ray can be irradiated in the course of dropping, to perform photo-polymerization.

As a target of gene introduction according to the method of the present invention, a plant having an established method to produce its protoplast and regeneration from the protoplast is preferable. More specifically, plants such as tomato, tobacco, rice and Arabidopsis can be exemplified. At first, protoplasts of these plants can be produced, and then they can be mixed with the bio-active beads. When the beads are suitably sized, an exogenous gene can be incorporated through endocytosis, and the exogenous genetic substance or the physiologically active compound contained in the beads can be released to exert their activity. For such a purpose, the particle size of the bio-active beads is preferably 1 $\mu$m to 0.01 $\mu$m. As an example of a target tissue, in which the beads are introduced, epidermal cells of onion or culture cells of tobacco can be adopted. Then, the exogenous genetic substance can be introduced by making pores using a technique of laser dissection. With regard to a plant of Solanaceae having large sieve pores or a plant of big tree such as crypomeria, the beads can be coated directly on the section of the plants. If the bio-active beads are suitably sized, the bio-active beads can be absorbed and transported toward the entire body of the plant. As a result, the physiologically active compound or the exogenous genetic substance can be released at the targeted parts. For such a purpose, a particle size of the bio-active beads is preferably less than 0.5 $\mu$m to 0.01 $\mu$m.

With regard to cultured cell derived from an animal, such as human being or Chinese hamster, incorporation can be performed by mixing with the bio-active beads, otherwise by phagocytosis depending on the size of bio-active beads. Then the exogenous genetic substance contained in the beads can be released to exert its activity. For such a purpose, a particle size of the bio-active beads is preferably less than 0.5 $\mu$m to 0.1 $\mu$m. Moreover, with regard to an animal individual, an exogenous genetic substance or a physiologically active compound can be included in beads having a size which enable administration through mucous membrane or oral administration. By administration of such bio-active beads, these substances can be introduced into the animal individual. For such a purpose, a particle size of the bio-active beads is preferably less than 1 $\mu$m.

The bio-active beads containing an exogenous genetic substance, that encodes a gene having a trait with economically benefit, can be mixed with yeast of spheroplast form. It can be introduced by endocytosis, depending on the size of the bio-active beads. Then the genetic substance contained in the bio-active beads can be released to exert its effect. For such a purpose, a particle size of the bio-active beads is preferably less than 1 mm to 0,01 mm.

The method of the present invention can be also used for introduction of a plant hormone into a plant. More specifically, auxin such as indol acetic acid or naphthalene acetic acid, cytokinin such as zeatin or kinetin, abscisic acid, gibberellin or peptide hormone can be introduced according to the present invention, in order to control growth of a plant. Moreover, antibiotics such as phytoalexins, more specifically, pisatin, phazeolin, medicarpin, licitin or licitinol can be also introduced into a plant, in order to achieve increased resistance toward bacteria. It is also possible to prepare individuals exhibiting increased stress resistance, such as UV stress, light stress and heavy metal stress, by adding an active oxygen scavenging agent such as phytokeratin and glutathione.

By the way, in the case that DNA is introduced at its naked form, distribution of DNA is attributed only to diffusion of DNA in a cell. Therefore, the probability of introduction into nucleus to achieve transformation is quite low. By using the bio-active beads of the present invention, the accumulated plasmid DNA within a bio-bead can be simultaneously introduced into a cell. Therefore, elevated transformation efficacy can be achieved. Moreover, by using a technique with optical tweezers, a genetic substance can be transported to a certain position of a cell, such as nucleus, which is necessary for gene expression.

For example, a plasmid DNA comprising cauliflower mosaic virus 35S promoter legated to glutathione gene can be prepared and said plasmid can be incorporated into the bio-active beads whereby introduced into plant cells. Here, cauliflower mosaic virus 35S promoter is a promoter generally used in the purpose to increase transcription of mRNA. In a plant thus produced, a large amount of glutathione can be produced in the cells. Then, the plant can eliminate heavy metals or poisons in the cells, owing to the effect of glutathione. Such plant has an ability to store heavy metals or poisons in environments in their cells, so that the plants can be used in the purpose to clean-up environment conditions. Moreover, constitutive expression of chitinase gene can be achieved in a plant. The gene encoding chitinase can be utilized, as chitinase exhibits the ability to decompose chitine, which is contained in cells of fungus or insects. The chitinase gene can be legated with a promoter which enable constitutive transcription of mRNA to construct a plasmid DNA, then the plasmid DNA can be incorporated into the bio-active beads and the bio-active beads can be introduced into useful plants. As a result, plants having resistance to diseases caused by fungi, such as mold, can be produced and improvement of productivity can be achieved, Moreover, the bio-active include mRNA of an effective gene and such beads can be introduced into cells at a high concentration. Such a technique would enable transient expression of the function of the gene. As a mRNA has an unstable nature, it will be totally decomposed in due time and characters of the mRNA will not remain. By utilizing such property, a gene having both characters of usefulness and toxicity, for example St gene, can be introduced into food crops in the form of mRNA at a high concentration. Introduction of such gene into food crops has some risk, because of its toxicity. However, by adopting technique described above, transient expression of the gene can be achieved, the product of the gene will not remain at the time of shipping the crop. Then, crop cultivation with high safety can be performed.

Moreover, the technique using plasmid DNA, only several genes can be introduced into cells at once. However, an artificial chromosome containing several tens to hundreds genes can be constructed, by using artificial chromosomes such as yeast artificial chromosome (YAC) or bacteria artificial chromosome (BAC). It is indicated that some prior techniques for production of beads utilizing emulsification have problems. For example, a high molecular weight DNA, such as an artificial chromosome, is likely to be decomposed by a shearing force accompanied by emulsification. However, according to the beads preparation technique of the present invention, DNA is incorporated into the beads after emulsification. Therefore, a high molecular weight DNA, such as an artificial chromosome, can be retained to the beads without causing damage to the DNA, and such beads can be introduced into cells. For example, high molecular weight artificial chromosome, encoding a series of enzymes necessary for metabolic pathway of C1 compounds such as methane or methanol, can be introduced into a plant to produce a novel plant. Such a novel plant can ingest C1 compounds and the C1 compounds can be utilized as a carbon source, though C1 compounds can not be metabolized by the native conventional plants and considered to exert rather poisonous effects.

Moreover, some wild plants are known to bear genes involved in resistant to diseases, cold damages or drought damages as well as QTL (quantitative trait loci) genes involved in increase of useful characters, which never exist in the present crop plants. In connection to it, following research has been in progress all over the world. That is, preparation of gene map of plants having these useful genes, determination of the position of the loci of the genes and cloning of the genes, resulting in introduction of the genes into crop plants. However, the operation to search such a gene one by one in order to perform cloning requires extremely large labor. As compared to this, in many cases, the chromosome on which the gene exists can be identified easily. Thus, a chromosome containing such gene can be isolated from the wild plant and it can be incorporated into beads according to the present invention at its intact form without causing any damage. As a result, the character of the gene can be introduced, without performing cloning of the gene.

Moreover, mitochondria and chloroplast, which are organelles of eukaryote, have their own individual genomic DNA, independently from the original genomic DNA of nucleus. In the genomes of these organelles, some loci of important genes determining characters of the living being are recognized to exist, like in the nucleus genuine. Techniques to isolate these organdies from cells have been developed for some plants. However, techniques to restore these organelles to the cells without any damage remains to be in the course of development. Thus, if an organelle can be trapped onto the bio-active beads of the present invention and introduced into a cell, its utility can be estimated to be high.

Moreover, in plants such as rice or sugar beet, the phenomenon of cytoplasmic male sterility has been known. In this phenomenon, failure on formation of normal pollen to cause sterility is observed, which is due to mutation of the gene on the mitochondria. However, when further mutation occurs on the nucleus gene, this phenomenon results in recovery of fertility. That is, fertility and sterility can be controlled by the combination of nucleus and mitochondria and it is effective in breed improvement of a plant and preservation of a plant breed. However, to alter the combination between nucleus and mitochondria, performance of intercross is generally required. In particular, as strains of male sterility can only be a maternal progenitor, its offspring necessarily have male sterility mitochondria due to maternal inheritance. If the wild type normal mitochondria can be trapped onto the beads of the present invention to be introduced into a cell, fertility can be recovered. Such technique will overcome present situation.

EXAMPLES

Example 1

(Introduction of the Bio-Active Beads by Electroporation)

Figure 2:
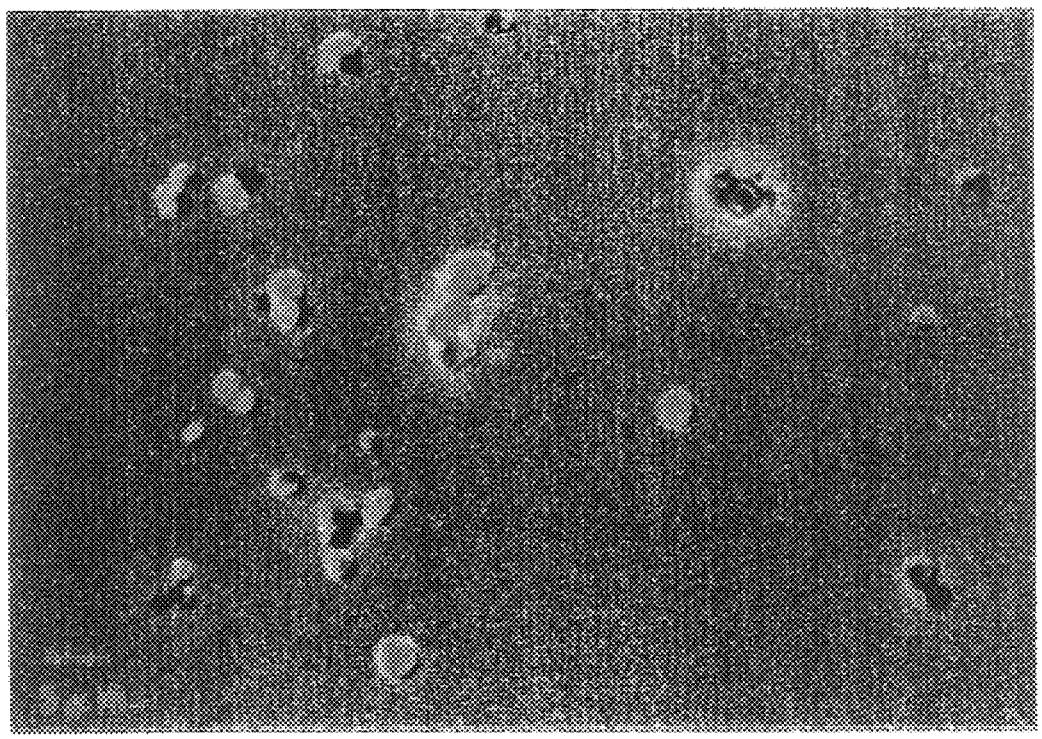
FIG. 2 is a photograph of plasmid DNA bound to bio-active beads, which was stained by YOYO-1 and detected by fluorescence.

In 100 µl of aqueous solution of sodium alginate (0.25 to 3%), which is the carrier of the beads, 900 µl of isoamyl alcohol was added. Under cooling condition, emulsion was formed using a handy sonicator for 10 to 15 seconds. Five hundreds µl of 25 to 1000 mM aqueous calcium chloride solution containing 0.1 mg/µl of plasmid DNA, harboring cauliflower mosaic virus 35S promoter and nopaline synthesis enzyme terminator sequence legated to green fluorescent protein gene, was added to the emulsion. Thereafter, vortex mixing was performed for about 1 minute and bio-active beads were prepared. The prepared bio-active beads were precipitated by centrifugation at 4000 rpm for 5 minutes using desktop-type micro-centrifuge and then recovered. The bio-active beads prepared by the present method had a concentration of 5 to $50 \times 10^5$ beads/ml and a diameter of 10 to 0.1 mm. In FIG. 1, a photograph of bio-active beads, which was taken by phase contrast microscope, is shown. It was stained by YOYO-1 fluorescent dye, and it was confirmed that the plasmid DNA was immobilized on the surface of the beads. In FIG. 2, a photograph of plasmid DNA trapped in the bio-active beads, which was stained by YOYO-1 and detected by fluorescence, is shown.

Figure 3:
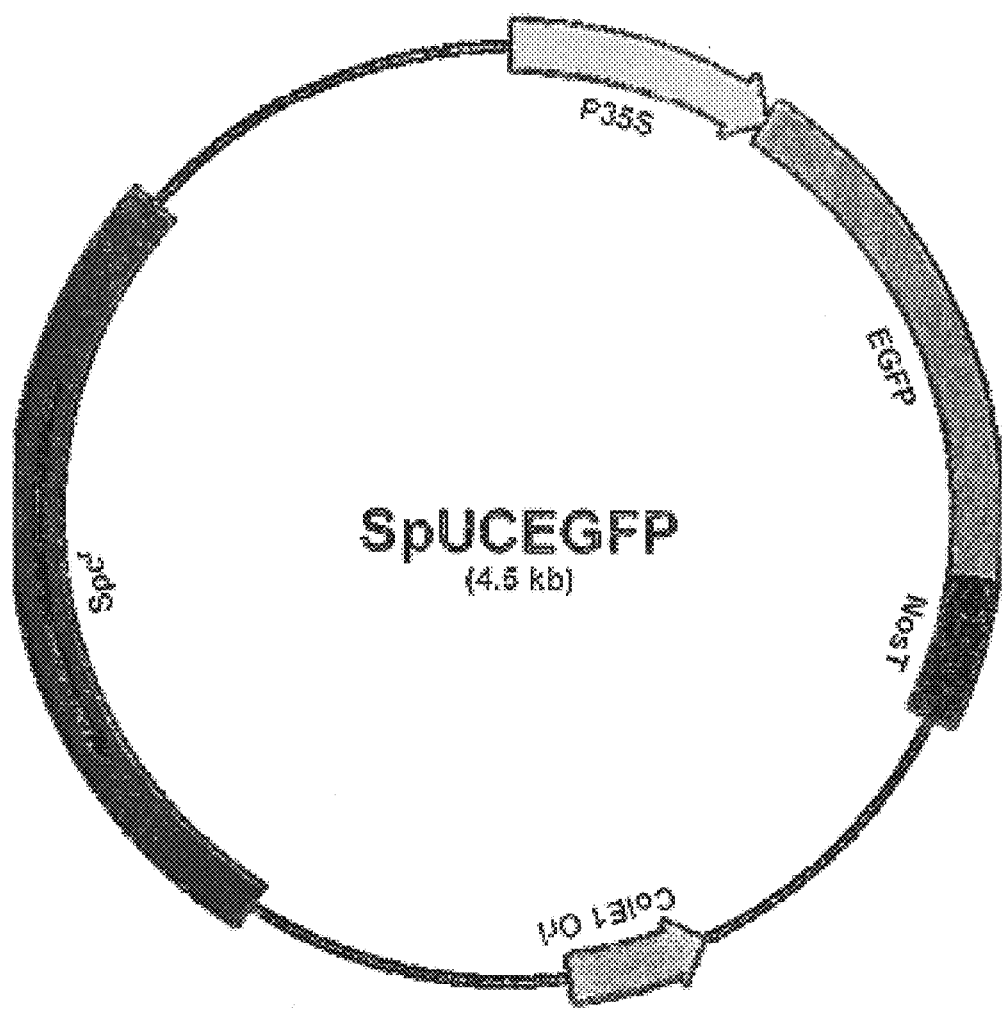
FIG. 3 is a schematic drawing showing construct of the prepared plasmid.
Figure 4:
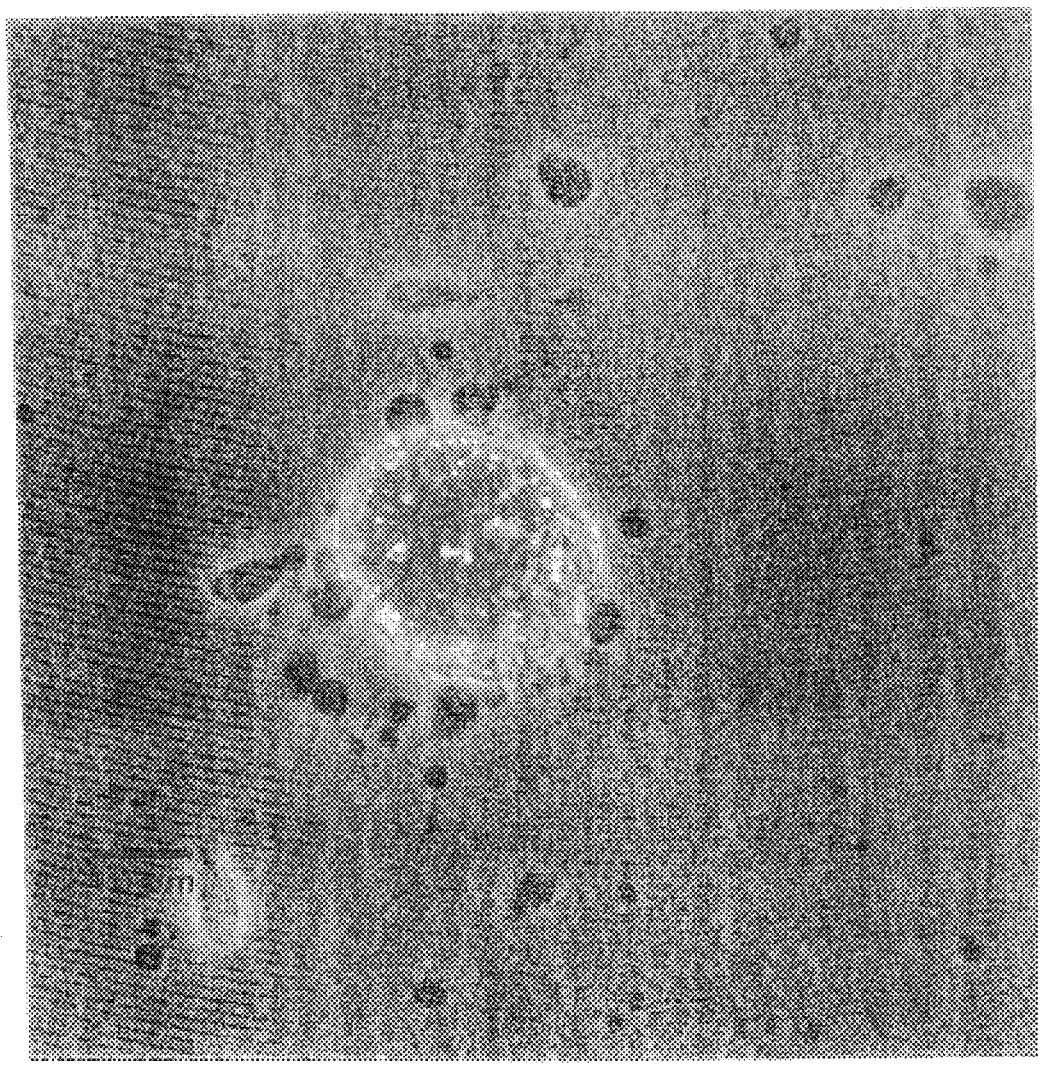
FIG. 4 is a photograph of green fluorescent protein expressed in protoplast of tobacco BY-2 cell introduced by electroporation, which was confirmed by fluorescence.

The plasmid DNA, harboring cauliflower mosaic virus 35S promoter and nopaline synthesis enzyme terminator sequence legated to green fluorescent protein gene, was thus prepared. The beads, in which the plasmid was introduced, was prepared according to the method of the present invention. The construct of the used plasmid is shown in FIG. 3. The beads ($1 \times 10^6$) containing the plasmid and tobacco protoplast culture cell BY-2 strain ($1 \times 10^4$) were mixed. Then electro-oration was performed using electrogene transfer system (available from Shimadzu, Japan) at rime constant of 200 µsec and voltage of 300 V, with a cuvette WITH a gap of 4 mm. As the buffer for electroporation, a solution of 5 mM MES, 17.5 mM $CaCl_2$, 0.3M mannitol (pH 5.8) was used. Incidentally, 70 mM of potassium chloride is conventionally used. However, calcium chloride was used here, in order to prevent sol formation of the beads. As a result, in the protoplast of BY-2 cell, in which beads retaining plasmid DNA was ingested, expression of green fluorescent protein was confirmed. The green fluorescent protein expressed in the protoplast of BY-2 cell was confirmed by fluorescence and the photograph is shown in FIG. 4.

Example 2

(Introduction of the Bio-Active Beads by Gene Transfer)

Furthermore, the bio-active beads were prepared according to the same method utilized in Example 1, using the plasmid described above. Then, the plasmid was introduced into tobacco BY-2 cells according to polyethylene glycol (PEG) mediated gene transfer. The tobacco protoplast culture cell BY-2 strain ($2 \times 10^6$) was suspended into PEG solution (mixture solution of 12% PEG 6000, 120 mM Calcium chloride, 0.4M mannitol). The suspension was mixed with the beads prepared in the above Example 1.

Figure 5:
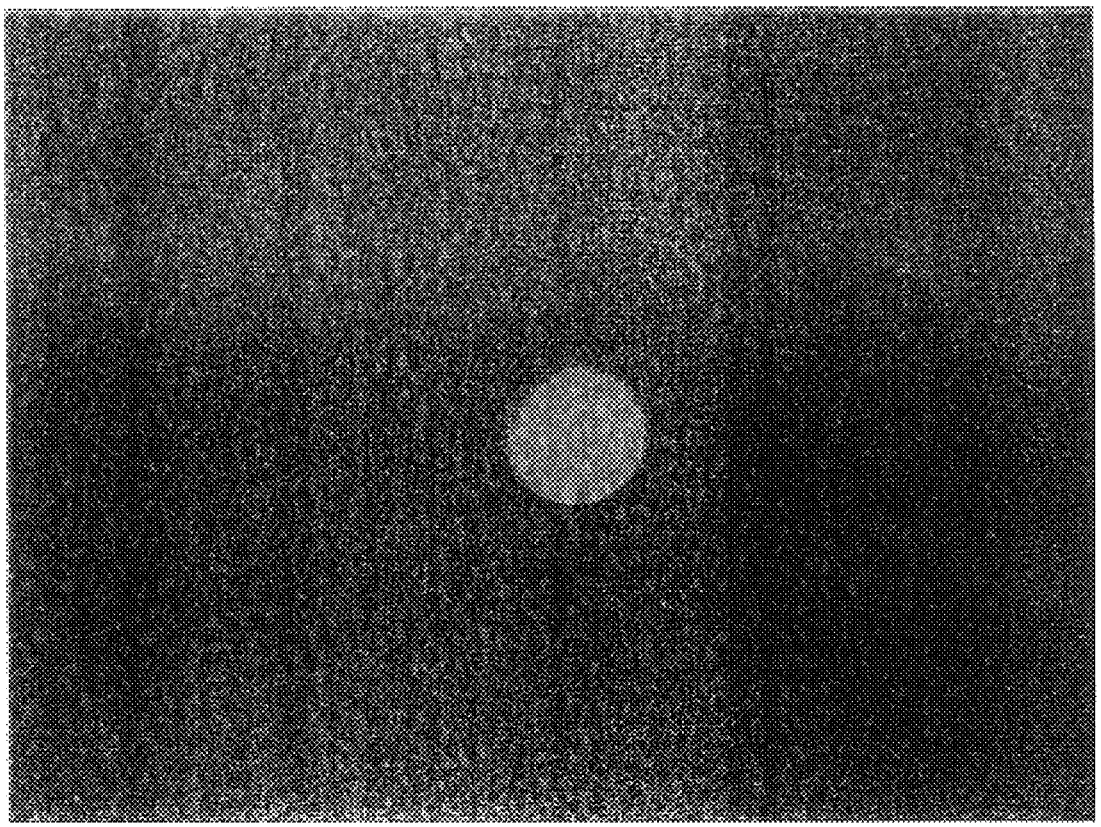
FIG. 5 is a photograph of green fluorescent protein expressed in protoplast of tobacco BY-2 cell, wherein the gene was introduced by the beads of calcium alginate with PEG-mediated gene transfer and the result was confirmed by fluorescence.

After mixing, it was stirred gently and settled for 30 min. Then it was centrifuged at 400 rpm for 3 min, the PEG solution was removed, 500 ml of culture medium (mixture solution of modified LS medium and 0.4M mannitol) was added and it was stirred gently. It was transferred to a culture dish of 35 mm diameter and cultured in dark for 1 day. The expression of green fluorescent protein was confirmed by fluorescence as shown in FIG. 5. It was revealed that transformation efficiency was higher than the conventional method and the maximum expression ratio reached to 0.0277%.

Example 3
(Preparation of Bio-Active Beads Including Chromosome or Nucleus)

Barley (2n=14) was synchronous cultured to accumulate cells at M-phase and a large amount of chromosome were obtained. The chromosome was fixed, then sorted using flow sorter was performed to fractionate a large amount of chromosome. The fractionated chromosome was ingested into the beads of calcium alginate. The synchronous cultivation, as well as sorting of nucleus and chromosome, was performed according to the method of Lysak et al. (Chromosome Res. 7 431–444 1999).
(Synchronous Cultivation of Barely)
(Synchronous Cultivation of Barely)

Seeds of barely were germinated by incubation in the dark at 25° C. for 2 days. The roots tips of the budded seeds were aerated for 18 hours and treated with 2.5 mM HU (hydroxyurea). As a result, most of the cells of the root tips accumulated at S-phase. Then, 6.5 hours of cultivation was performed in the absence of HU. By this treatment, cells accumulated at S-phase re-entered to the cell cycle and the cells went to G2-phase, then to M-phase. In order to accumulate cell cycle at M-phase, the cells were treated by 2.5 $\mu$M of APM (amiprophos-methyl) for 2 hours. Then they were immersed into ice water to enhance dispersion of chromosome in the cells.
(Preparation of Chromosome Suspension)

To retain the shape of chromosomes, treatment by 2% formaldehyde was performed for 20 min for fixation of the cells. Then washing using Tris buffer for 5 min was repeated for three times. Root tips (25–30 pcs) were cut off and the cells of the root tips were disrupted using polytron homogenizer. After disruption, residues of the cell were removed using nylon mesh.
(Sorting)

Sorting was performed using FAGSVantage flow cytometer (Beckton Dickinson, USA) equipped with an argon-ion laser. To improve sensitivity of flow cytometer, CV (coefficient of variation) was adjusted to less than 2.0%, prior to analysis. To analyze relative fluorescent intensity of the isolated chromosome and nucleus, the system threshold was set on the fluorescent pulse height (LF1-H). The isolated chromosome was stained with 4'6'-diamidino-2-phenylindole (DAPI) at a final concentration of 2.0 $\mu$g/ml. To avoid excess damage after performance of sorting, the chromosome was directly fractionated into eppendorff tubes containing 33 $\mu$l of 1.5% sodium alginate. As a result, sorting of 40,000 pcs of chromosomes was achieved.
(Preparation of Bio-Active Beads)

Figure 6:
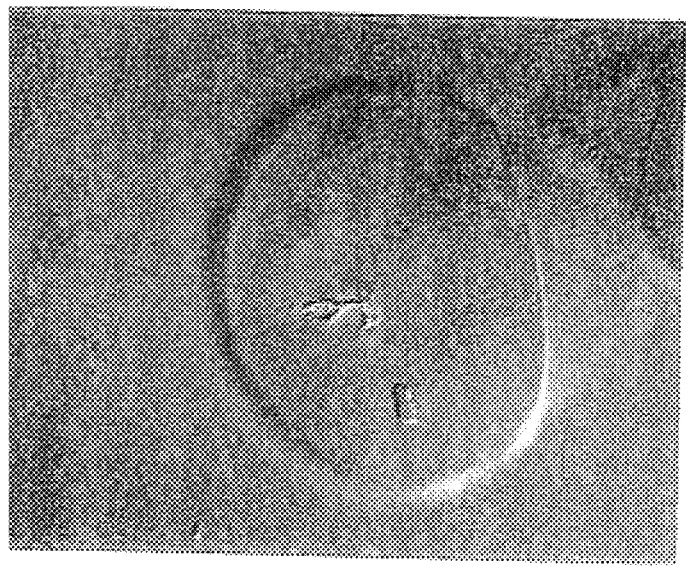
FIG. 6 is a photograph of chromosome incorporated into beads of calcium alginate, which was confirmed by DAPI staining.

To a solution of alginate (final concentration of about 0.5%) containing chromosome, isoamyl alcohol was added and stirred sufficiently using a vortex mixer. Then 100 mM calcium chloride solution was added immediately and the emulsion of alginate was solidified. Isoamyl alcohol was removed by centrifugation and washing operation using 100 mM calcium chloride was repeated 4 times or more. The big-active beads including chromosome was thus prepared and they were shown in FIG. 6. According to FIG. 6, chromosomes stained by DAPI are observed in bio-active beads of calcium alginate, which can be recognized by blue fluorescence.

Figure 7:
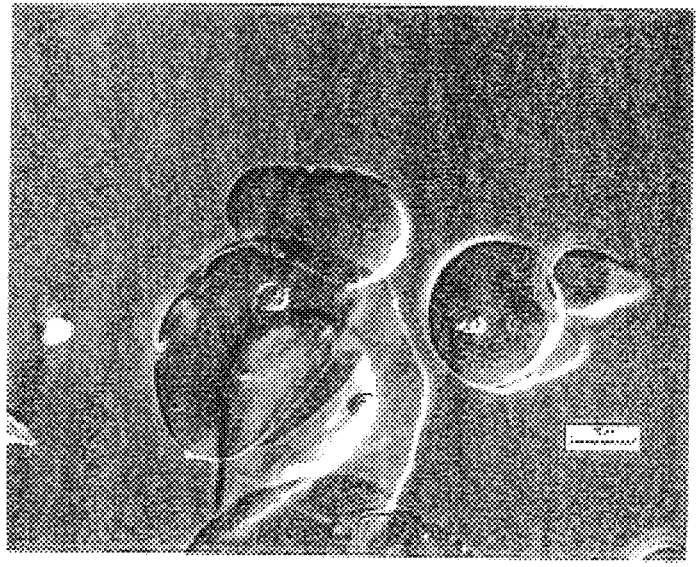
FIG. 7 is a photograph of nuclei incorporated into beads of calcium alginate, which was confirmed by DAPI staining.

Furthermore, sorting of nuclei was performed using the same procedure, and bio-active beads including nuclei could be also prepared. The bio-active beads including nuclei were shown in FIG. 7. According to FIG. 7, nuclei stained by DAPI are observed in bio-active beads of calcium alginate, which can be recognized by blue fluorescence.

According to the present invention, a novel method for introduction of an exogenous genetic substance or a physiologically active compound of large size was provided.

What is claimed is:

1. A method for producing a bio-active bead with a genetic substance or a physiologically active compound comprising the steps of:
   preparing an emulsion of water-in-oil type containing a solidification material in the water phase,
   adding an aqueous solution to the emulsion, the aqueous solution containing a solidification agent and at least one of said genetic substance and said physiologically active compound;
   forming a bio-active bead as the resulting solidification product; and
   immunobilizing said genetic substance or said physiologically active compound to said bead, wherein the bead has the shape of a sphere fine particle with a diameter of 0.01 mm to 10 mm.

2. A method for producing a bio-active bead with a genetic substance or a physiologically active compound, the method comprising the steps of:
   forming a water drop containing a solidification agent and at least one of said genetic substance and said physiologically active compound using a cell sorter;
   dropping said water drop into an aqueous solution of a solidification material and;
   forming said bio-active head as the resulting solidification product.

3. The method according to claim 1, wherein said bead is a bead comprising calcium alginate.

4. The method according to any one of claims 1, 2 or to 3 wherein said genetic substance is selected from the group consisting of mRNAs, plasmid DNAs, chromosomes, artificial chromosomes, organelle DNAs and nucleus.

5. The method according to any one of claims 1, 2 or to 3, wherein said physiologically active compound is selected from the group consisting of plant hormones, antibiotics, and active oxygen scavenging agents.

6. A method for introduction of an exogenous genetic substance or a physiologically active compound into a cell, the method comprising introduction of the bio-active bead produced by the method according to any of the claims 1, 2 or to 3.

7. A method of producing a bio-active bead, the beads having a shape of a sphere fine particle with a diameter of 0.01 $\mu$m to 10 $\mu$m, the method comprising the steps of:
   preparing an emulsion of water-in-oil type containing sodium alginate, as a solidification material, in the water phase;
   adding an aqueous solution to the emulsion, the aqueous solution containing calcium chloride, as a solidification agent, and at least one genetic substance and or physiologically active compound and;
   forming said bio-active bead as the resulting calcium alginate as a solidification product.

8. A method of producing a bio-active bead, the beads having a shape of a sphere fine particle with a diameter of 0.01 μm to 10 μm, the method comprising the steps of:

forming a water drop containing calcium cloride, as a solidification agent, and at least one genetic substance or physiologically active compound using a cell sorter;

dropping said water drop into an aqueous solution of sodium alginate, as a solidification material, and;

forming said bio-active bead as the resulting calcium alginate as a solidification product.

* * * * *